United States Patent
Eibl et al.

(10) Patent No.: US 9,980,907 B2
(45) Date of Patent: May 29, 2018

(54) THERMOLABILE LIPOSOME WITH A CONTROLLED RELEASE TEMPERATURE

(75) Inventors: Hansjörg Eibl, Bovenden (DE); Lars H. Lindner, Munich (DE)

(73) Assignee: Max-Planck-Gesellschaft zur Förderung der Wissenschaften e.V., Munich (DE)

( * ) Notice: Subject to any disclaimer, the term of this patent is extended or adjusted under 35 U.S.C. 154(b) by 0 days. days.

(21) Appl. No.: 12/817,229

(22) Filed: Jun. 17, 2010

(65) Prior Publication Data

US 2010/0254909 A1  Oct. 7, 2010

Related U.S. Application Data

(62) Division of application No. 10/527,222, filed as application No. PCT/EP03/10163 on Sep. 12, 2003, now abandoned.

(30) Foreign Application Priority Data

Sep. 12, 2002 (DE) ................................ 102 42 367

(51) Int. Cl.
*A61K 9/127* (2006.01)

(52) U.S. Cl.
CPC .................... *A61K 9/127* (2013.01)

(58) Field of Classification Search
USPC ........................................................ 424/450
See application file for complete search history.

(56) References Cited

U.S. PATENT DOCUMENTS

| 5,436,234 | A * | 7/1995 | Eibl ............................... 514/77 |
| 5,720,876 | A * | 2/1998 | Mackrle et al. ............. 210/197 |
| 6,284,267 | B1 | 9/2001 | Aneja |
| 6,413,543 | B1 | 7/2002 | Eibl |
| 6,726,925 | B1 * | 4/2004 | Needham ...................... 424/450 |
| 7,709,464 | B2 | 5/2010 | Eibl |
| 2002/0102298 | A1 * | 8/2002 | Needham ...................... 424/450 |
| 2004/0137048 | A1 | 7/2004 | Eibl |
| 2004/0247659 | A1 | 12/2004 | Eibl |
| 2009/0004258 | A1 * | 1/2009 | Yang et al. ................... 424/450 |

FOREIGN PATENT DOCUMENTS

| DE | 196 22 224 | 8/1997 |
| JP | 06227966 | * 8/1994 |
| WO | WO 99/52505 | 10/1999 |
| WO | WO 02/064116 | 8/2002 |
| WO | WO 03/026617 | 4/2003 |

OTHER PUBLICATIONS

Maruyama K, et al, International Journal of Pharmaceutics, vol. 111, pp. 103-107, 1994.*
Hossann, et al. "In vitro stability and content release properties of phosphatidylglyceroglycerol containing thermosensitive liposomes", *Biochim. and Biophys.* 1768 (2007), pp. 2491-2499.
Lindner, et al. "Novel Temperature-Sensitive Liposomes with Prolonged Circulation Time", Clinical Cancer Research, vol. 10 (2004), pp. 2168-2178.
Fabiana Ganz "Cholesteryl-Phosphoglycerine".

* cited by examiner

*Primary Examiner* — Gollamudi Kishore
(74) *Attorney, Agent, or Firm* — Rothwell, Figg, Ernst & Manbeck, P.C.

(57) ABSTRACT

The invention relates to a thermolabile liposome with a controlled release temperature for the liposome content, in particular a liposome which is stable at 37° C. in serum and with a controlled release temperature of between 40 and 80° C.

4 Claims, 4 Drawing Sheets

\* ≙ comparison example

THERMOLABILE LIPOSOME WITH A CONTROLLED RELEASE TEMPERATURE

This application is a divisional application of U. S. Serial No; Ser. No. 10/527,222 filed Dec. 21, 2005, now abandoned incorporated herewith by reference in its entirety, which is a § 371 of PCT/EP2003/010163 filed Sep. 12, 2003, which claims priority from German Patent Application No. 102 42 367.9 filed Sep. 12, 2002.

The invention relates to a thermolabile liposome with a controlled release temperature for the liposome content, in particular a liposome which is stable at 37° C. in serum and with a controlled release temperature of between 40 and 80° C.

Liposomes are artificially formed vesicles consisting of lipid bilayers which enclose an aqueous compartment (Bangham et al., 1965). Originally also utilized as a model system for a cell membrane, liposomes have recently been developed further, especially for pharmaceutical transport. Liposomes can increase the tolerability of active compounds here (lowering of the active toxicity of amphothericin B by liposomal formulation (AmBisome®) by a factor of 75 (Proffitt et al., 1991)). However, they also increase the possibility of transporting pharmaceuticals specifically into diseased tissue (Forssen et al., 1992). After intravenous administration, liposomes are mainly absorbed in cells of the reticuloendothelial system (RES) of the liver and spleen (Gregoriadis and Nerunhun, 1974). In order to be able to utilize liposomes as pharmaceutical vehicles for cells outside the RES, it was attempted to increase the circulation time of the liposomes in the blood. Especially in tumors, which are often very highly vascularized (Jain, 1996) and whose vessels are particularly permeable due to dilated interendothelial connections, a large number of fenestrations, and discontinuous basal membranes (Murray and Carmichael, 1995), the probability of absorption of liposomes would be massively increased thereby.

A first problem in the use of liposomes for the transport of active compounds or labelling substances in body fluids therefore lies in the increase in the circulation time in the serum. Indeed, it has already been found that due to covalent bonding of methoxy-polyethylene glycols to the liposomal membrane the premature recognition of the liposomes by the RES is prevented and thus the circulation time of the liposomes can be improved. In addition to an improvement in the circulation time, however, there is also great interest in a possibility of achieving a controlled release of the liposome ingredients at a certain temperature by means of the action of temperature.

The invention is therefore based on the object of making available a liposome which has a significantly improved half-life in the serum, compared with the customary half-life of known liposomes of the order of magnitude of around 4 hours, and which is constituted such that the content of the liposomes is rapidly released at a certain temperature.

This object is achieved according to the present invention by means of a liposome with a controlled release temperature for the liposome content, which is characterized in that it is essentially formed from at least one phosphatidylcholine with a main transition temperature in the range from 0 to 80° C. and more than to 70% by weight of phosphatidyloligoglycerol. According to an older proposal, it was only possible to obtain liposomes having a maximum phosphatidyloligoglycerol content of 15% by weight. Now, however, it has surprisingly been found that it is possible to increase the phosphatidyloligoglycerol content up to 70%, so that the range of the achievable release temperatures of the liposomes is extended even more, but especially the half-lives are again improved.

According to a preferred embodiment, the liposomes according to the invention additionally contain smaller amounts of alkylphosphocholines, preferably 10 to 15% by weight. Suitable substances are, for example, hexadecylphosphocholine, oleylphosphocholine and ether lysolecithins. In the ether lysolecithins, the hydroxyl group in position 2 of the glycerol can be methylated or free. In this embodiment, it is possible to increase the release of the substances enclosed in the liposome from approximately 70% without increasing the content of alkylphosphocholine to virtually 100%, which is to be attributed to an acceleration of liposome opening. In addition, the alkylphosphocholines have an antitumor effect due to temperature-dependent release from the liposomes.

Liposomes constructed according to the invention have significantly improved half-lives of up to more than 25 hours in the serum and the content(s) can be rapidly and completely released at a predetermined temperature by suitable choice of the components and amounts of the components as a function of their main transition temperature.

Preferably, the liposome according to the invention is composed of approximately 20 to 75% by weight of dipalmitoyllecithin(1,2-dipalmitoylglycero-3-phosphocholine), approximately 10 to 25% by weight of distearoyllecithin(1,2-distearoylglycero-3-phosphocholine) and more than 15 to approximately 50% by weight of dipalmitoylphosphoglyceroglycerol. Such a preferred composition is stable at 37° C. in the serum, but rapidly releases the content on exceeding a temperature of 40° C.

A further preferred composition with an improved release of the substances enclosed in the liposome consists of approximately 15 to 70% by weight of dipalmitoyllecithin, approximately 10 to 25% by weight of distearoyllecithin and more than 15 to approximately 45% by weight of dipalmitoylphosphoglyceroglycerol.

The abovementioned preferred composition of the liposome according to the invention can be tailor-made for other temperature ranges by choice of components with the main transition temperature suitable in each case. In table 1, the main transition temperatures ($T_M$) of phosphatidylcholines whose main transition temperatures lie in the range from 0 to 80° C. are indicated. The main transition temperatures are, as can be seen from the table, dependent on the chain length and the distribution on positions 1 and 2 of glycero-3-phosphocholine or on positions 1 and 3 of glycero-2-phosphocholine.

TABLE 1

| $T_M$ | Phosphatidylcholine |
|---|---|
| 5° C. | 1-palmitoyl-2-oleoyl- |
| 7° C. | 1-stearoyl-2-oleoyl- |
| 11° C. | 1-palmitoyl-2-lauroyl- |
| 14° C. | 1-behenoyl-2-oleoyl- |
| 17° C. | 1-stearoyl-2-lauroyl- |
| 19° C. | 1,3-dimyristoyl- |
| 23° C. | 1,2-dimyristoyl- |
| 27° C. | 1-palmitoyl-2-myristoyl- |
| 33° C. | 1-stearoyl-2-myristoyl- |
| 37° C. | 1-myristoyl-2-palmitoyl- |
| 39° C. | 1,3-dipalmitoyl- |
| 41° C. | 1,2-dipalmitoyl- |
| 42° C. | 1-myristoyl-2-stearoyl- |
| 46° C. | 1-stearoyl-3-myristoyl- |
| 48° C. | 1-stearoyl-2-palmitoyl- |

TABLE 1-continued

| $T_M$ | Phosphatidylcholine |
|---|---|
| 52° C. | 1-palmitoyl-2-stearoyl- |
| 53° C. | 1,3-distearoyl- |
| 56° C. | 1,2-distearoyl- |
| 66° C. | 1,2-diarachinoyl- |
| 75° C. | 1,2-dibehenoyl- |
| 80° C. | 1,2-dilignoceroyl- |

The values presented in table 1 show that virtually any desired temperature in the indicated range from 0 to 80° C. can be adjusted by use of fatty acids with an uneven chain length and suitable distribution on the glycerol parent structure.

The content of phosphatidyloligoglycerols in the liposome according to the invention is essential for the long circulation time in the serum which is necessary. Phosphatidyloligoglycerols and their preparation are disclosed in DE 196 22 224. Preferably, dipalmitoylphosphoglyceroglycerol (DPPG2) is used.

The thermolabile liposomes according to the invention are outstandingly suitable for use in various fields, but in particular in regional deep hyperthermia. Regional deep hyperthermia, which is used in combination with systemic chemotherapy in specialized clinical centers, presents itself as an ideal technique for tumor-specific liposomal transport and the subsequent release of a pharmaceutical from the liposomal shell. Thus, hyperthermia, on the one hand, promotes the extravasation of liposomes from tumor capillaries into the interstitium (Gaber et al., 1996). On the other hand, a release of the pharmaceutical from special thermosensitive liposomes can be induced by heating (Magin and Niesman, 1984). Additionally, there are numerous indications of an increased cytotoxic effect of cytostatics (Hahn et al., 1975), and of an immunomodulation (activation of NK cells; Multhoff et al., 1999) by regional deep hyperthermia.

The thermolability of the liposomes according to the invention is caused by the phase transition of the phospholipids within the liposome membrane. If the phase transition temperature is passed through, a short-term membrane instability and subsequent release of the liposomal content occur.

In the abovementioned regional hyperthermia, the tumor is specifically overheated regionally, so that the temperature rises above the threshold temperature for the release of the liposome content. Possible liposome contents here are in particular active compounds which can be used in oncology, such as, for example, cytostatics. However, contrast agents, for example gadolinium, e.g. Magnevist®, Multihance® or Omniscan®, carboxyfluorescein, iodine-containing contrast agents which are derived from pyridines or aromatic carboxylic acids, or the like on their own or together with an active compound can also be released. The temperature-dependent release of gadolinium from the liposomes can be shown with the aid of MRT by means of a modified T1 time (0.2 or 1.5 Teslar respectively). By use of contrast agents, such as gadolinium, noninvasive thermometry is made possible in which the temperature reached can be determined by MRC, which measures the gadolinium released. In this use of the liposomes according to the invention, a hyperthermia apparatus coupled with an MRC apparatus is expediently used. Use of liposomes with iodine-containing contrast agents for demonstration in computer tomography (for example for the thermoablation of liver metastases) is also conceivable.

A further type of use for the liposomes according to the invention is found in ophthalmology. On encapsulation of a fluorescent labeling substance, it can be demonstrated where the desired overheating has actually occurred, for example, in a laser treatment by release of the fluorescent active compound, such as, for example, carboxyfluorescein.

Analogously to the illustrated possibility of use in the eye, liposomes according to the invention can therefore be generally used for the purpose of making temperatures reached additionally determinable, e.g. if certain heating temperatures or the like are to be ascertained.

The liposomes according to the invention consist essentially of the substances indicated above, which are preferably present in pure form. Impurities should be kept as low as possible, in particular a cholesterol content which is as low as possible should be present. Liposomes which are completely free of cholesterol are preferred, since cholesterol leads to a spreading of the phase transition temperature and thus to a thermal transition range which is too broad.

The thermolabile liposomes according to the invention are prepared in the customary manner by dissolving the lipids, e.g. in chloroform or chloroform/water/iso-propanol, stripping off the solvent, expediently in vacuo in a rotary evaporator, and temperature-controlling the lipids with aqueous solutions of the ingredients to be encapsulated at temperatures which lie above the phase transition temperature. The duration of this temperature treatment is expediently 30 to 60 minutes, but can also be shorter or longer. By means of freezing-thawing processes which are repeated a number of times, for example freezing and thawing again 2 to 5 times, homogenization takes place. Finally, the lipid suspension obtained is extruded through a membrane of defined pore size at a temperature above the phase transition temperature in order to achieve the desired liposome size. Suitable membranes are, for example, polycarbonate membranes of defined pore size, such as 100 to 200 nm. Finally, nonencapsulated ingredient can optionally be separated off, for example by column chromatography or the like.

The following figures and examples illustrate the invention further.

FIG. 1 shows the obtained values of the in vitro CF release from thermolabile liposomes.

DPPC:DSPC:DPPG2=5:2:3    Liposome Composition:

Great stability in the presence of serum at 37 C (CF release after 18 hours <7%).

Figure 1:
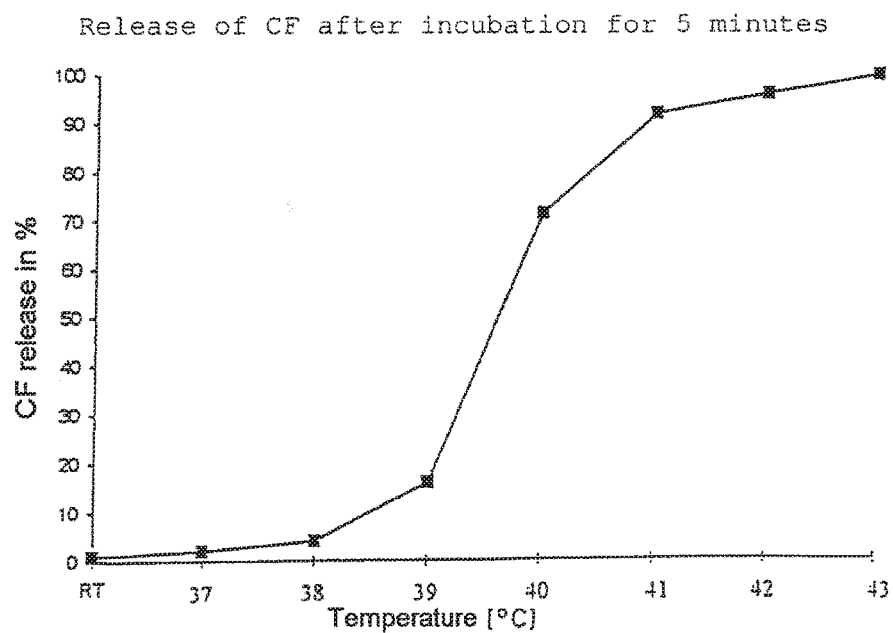

EXAMPLE 1 a) The Liposomes Presented in Table 2 are Prepared in the Manner Described Above.

TABLE 2

| | | |
|---|---|---|
| DPPG$_2$ 30% | DSPC 0% | DPPC 70% |
| DPPG$_2$ 30% | DSPC 10% | DPPC 60% |
| DPPG$_2$ 30% | DSPC 20% | DPPC 50% |
| DPPG$_2$ 30% | DSPC 30% | DPPC 40% |

TABLE 2-continued

| | | | |
|---|---|---|---|
| DPPG₂ 10% | DSPC 0% | DPPC 90% | |
| DPPG₂ 10% | DSPC 10% | DPPC 80% | |
| DPPG₂ 10% | DSPC 20% | DPPC 70% | |
| DPPG₂ 10% | DSPC 30% | DPPC 60% | |
| DPPG₂ 0% | DSPC 20% | DPPC 80% | |
| DPPG₂ 10% | DSPC 20% | DPPC 70% | |
| DPPG₂ 20% | DSPC 20% | DPPC 60% | |
| DPPG₂ 30% | DSPC 20% | DPPC 50% | |
| DPPG₂ 40% | DSPC 20% | DPPC 40% | |
| DPPG₂ 50% | DSPC 20% | DPPC 30% | |
| DPPG₂ 80% | DSPC 20% | DPPC 0% | |
| DSPG₂ 10% | | DPPC 90% | |
| DSPG₂ 20% | | DPPC 80% | |
| DSPG₂ 30% | | DPPC 70% | |
| DSPG₃ 10% | | DPPC 90% | |
| DSPG₃ 20% | | DPPC 80% | |
| DPPG₂ 30% | DSPC 20% | DPPC 40% | 1PPC 10% |
| DPPG₂ 30% | DSPC 20% | DPPC 30% | 1PPC 20% |
| DSPG₂ 20% | | DPPC 70% | 1SPC 10% |
| DSPG₂ 20% | | DPPC 60% | 1SPC 20% |
| DSPG₂ 20% | | DPPC 70% | hexadecyl-PC 10% |
| DSPG₂ 20% | | DPPC 60% | hexadecyl-PC 20% |
| DSPG₂ 20% | | DPPC 70% | octadecyl-PC 10% |
| DSPG₂ 20% | | DPPC 60% | octadecyl-PC 20% |
| DSPG₂ 10% | | DPPC 80% | Et-18 OCH₃PC 10% |
| DSPG₂ 10% | | DPPC 70% | Et-18 OCH₃PC 20% |
| DSPG₂ 10% | | DPPC 60% | Et-18 OCH₃PC 30% |

Abbreviations:
DPPC = 1,2-dipalmitoyl-sn-glycero-3-phosphocholine
DSPC = 1,2-distearoyl-sn-glycero-3-phosphocholine
DPPG₂ = 1,2-dipalmitoyl-sn-glycero-3-phospho-diglycerol
DSPG₂ = 1,2-distearoyl-sn-glycero-3-phospho-diglycerol
DSPG₃ = 1,2-distearoyl-sn-glycero-3-phospho-triglycerol
1PPC = 1-palmitoyl-sn-glycero-3-phosphocholin
1SPC = 1-stearoyl-sn-glycero-3-phosphocholine
Et-18 OCH₃PC = 1-octadecyl-2-methylglycero-3-phosphocholine They contain encapsulated carboxyfluorescein. Free carboxyfluorescein was separated off beforehand by column chromatography using Sephadex G75.

b) Chamber Model:

The Syrian hamster chamber model (A-Mel-3 melanoma of the Syrian hamster) is suitable for the intravital microscopic detection of the carboxyfluorescein (CF) release from thermolabile liposomes in the hyperthermia field. In this, a transparent, dorsal skin chamber is implanted in a Syrian golden hamster. After implantation of the skin chamber, the implantation of cells of the hamster A-Mel-3 melanoma takes place on the subcutaneous tissue located in the chamber. Within a few days, a tumor several millimeters in size grows within the dorsal skin of the hamster. The microcirculation and the fluorescence enrichment within the tumor can be observed using a modified vital microscope. The animals are additionally given a central venous catheter. With the aid of a heat exchanger located under the skin chamber, heating of the tumor to 42° C. can be achieved locally. The tumor temperature can be measured directly with the aid of a temperature probe (Endrich, 1988).

In addition to vital microscopy, the process of MRT measurement in the chamber model is also established (Pahernik et al., 1999). In this, MRT images can be recorded analogously to microscopy.

Figure 2:
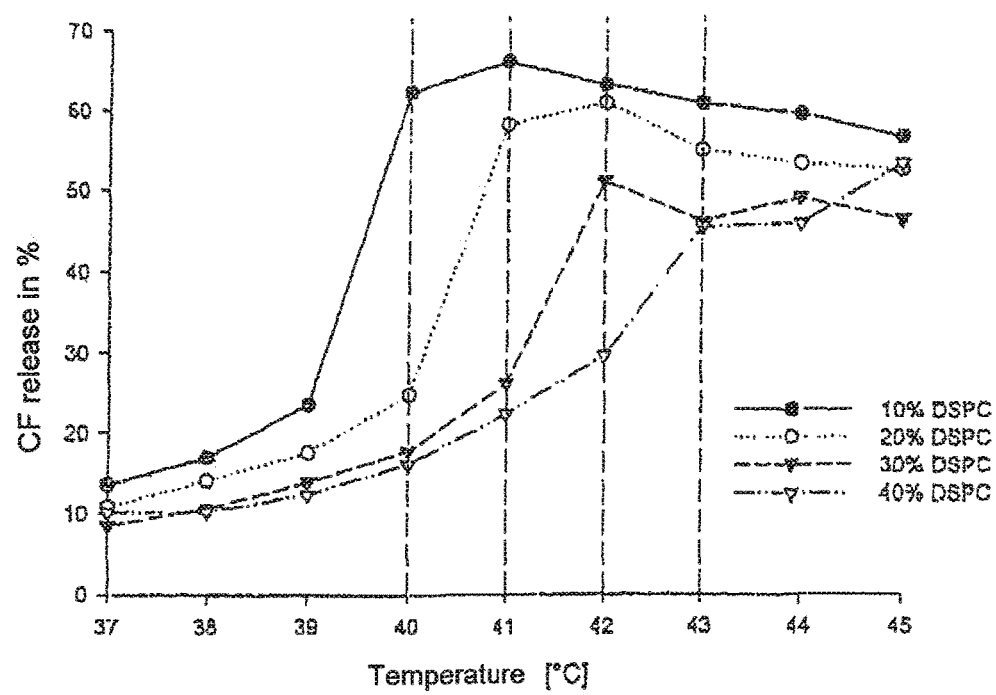
FIG. 2 shows the influence of the release temperature of DPPG$_2$/DSPC/DPPC liposomes by variation of the proportion of DSPC at the expense of DPPC.
Figure 3:
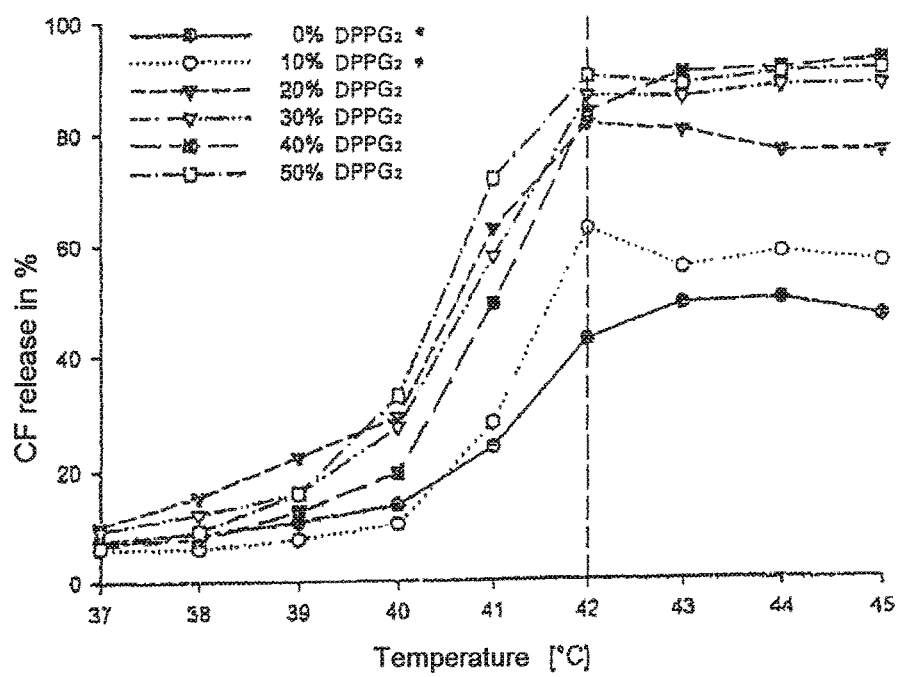
FIG. 3 shows the improvement in the CF release from DPPG$_2$/DSPC/DPPC liposomes by increasing the proportion of DPPG$_2$ at the expense of DPPC (constant proportion of DSPC at 20%).
Figure 4:
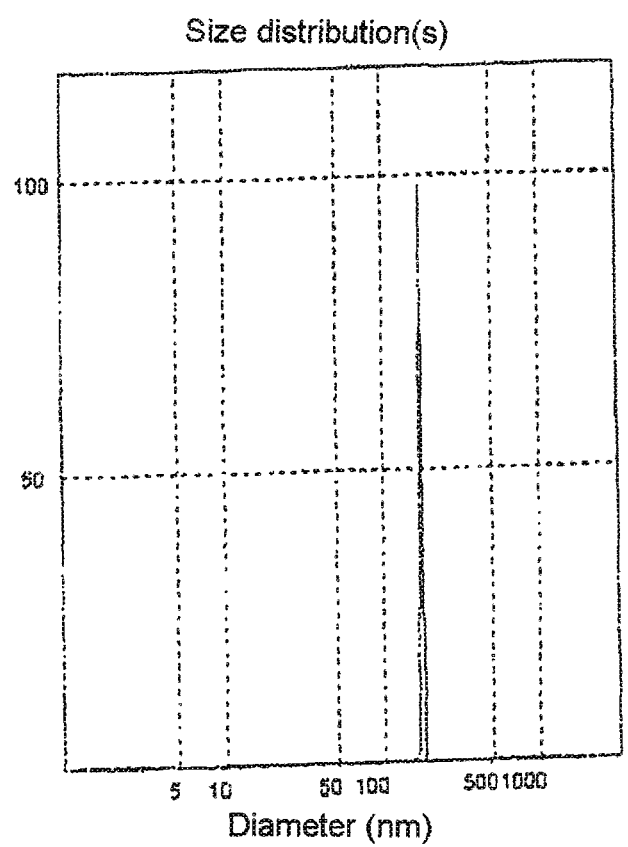
FIG. 4 shows the photon correlation spectroscopy (PCS) of liposomes consisting of 30% by weight of DPPG$_2$, 20% by weight of DSPC and 50% by weight of DPPC (mean size: 175 nm).

The obtained values of the in vitro CF release are shown in FIG. 1. Furthermore, the influence of the release temperature of DPPG₂/DSPC/DPPC liposomes by variation of the proportion of DSPC at the expense of DPPC is shown in FIG. 2. The improvement in the CF release from DPPG₂/DSPC/DPPC liposomes by increasing the proportion of DPPG₂ at the expense of DPPC (constant proportion of DSPC at 20%) is shown in FIG. 3. Moreover, photon correlation spectroscopy of DPPG₂/DSPC/DPPC liposomes is shown in FIG. 4.

The invention claimed is:

1. A method for temperature controlled release of liposome contents from a thermolabile liposome in the region of a tumor,
   wherein the thermolabile liposome consists essentially of
   a) from 20 to 75% by weight of dipalmitoyl-phosphatidylcholine and from 10 to 25% by weight of distearoyl-phosphatidylcholine, and
   b) from 21.5-32 by weight of dipalmitoylphosphodiglycerol and no cholesterol,
   wherein said thermolabile liposome is stable at 37° C. and has a release temperature of 40° C. or higher;
   wherein the liposome contents comprise doxorubicin, gemcitabine or a gadolinium based contrast agent,
   comprising intravenously administering said thermolabile liposome, and
   changing temperature in the region of a tumor to above 40° C. to achieve a rapid release of the liposome content in the region around said tumor.

2. The method as claimed in claim 1, wherein said thermolabile liposome has a release temperature of 41° C. or higher and
   wherein the temperature is changed to above 41° C. to achieve a release of the liposome content.

3. A method for release of liposome contents in the region of a tumor, wherein said liposome contents are released from a thermolabile liposome having a controlled temperature for releasing the liposome contents, comprising
   administering said thermolabile liposome to a patient in need of such treatment, and
   changing the temperature in the region of a tumor to above 40° C. to achieve a release of the liposome contents in the region of the tumor,
   wherein said thermolabile liposome consists essentially of from 20 to 75% by weight of dipalmitoyl-phosphatidylcholine, from 10 to 25% by weight of distearoyl-phosphatidylcholine and from 21.5 to 32% by weight of dipalmitoylphosphodiglycerol, and no cholesterol,
   wherein the thermolabile liposome is stable at 37° C. and has a release temperature of 40° C. or higher,
   and wherein the liposome contents comprise doxorubicin, gemcitabine or a gadolinium based contrast agent,
   comprising the steps of administering said thermolabile liposome by intravenous administration, and
   changing the temperature in the region of a tumor to above 40° C. to achieve a rapid release of the liposome contents in the region of the tumor.

4. The method as claimed in claim 3, wherein said thermolabile liposome has a release temperature of 41° C. or higher and
   wherein the temperature is changed to above 41° C. to achieve a release of the liposome content.

* * * * *